(12) United States Patent
Sebastian (10) Patent No.: US 11,850,344 B2
(45) Date of Patent: Dec. 26, 2023

(54) GAS BUBBLE SENSOR

(71) Applicant: Mozarc Medical US LLC, Minneapolis, MN (US)

(72) Inventor: Subin Sebastian, Kattappana (IN)

(73) Assignee: Mozarc Medical US LLC, Minneapolis, MN (US)

( * ) Notice: Subject to any disclaimer, the term of this patent is extended or adjusted under 35 U.S.C. 154(b) by 4 days.

(21) Appl. No.: 17/399,606

(22) Filed: Aug. 11, 2021

(65) Prior Publication Data
US 2023/0046703 A1    Feb. 16, 2023

(51) Int. Cl.
*A61M 1/36* (2006.01)
*A61M 1/28* (2006.01)

(52) U.S. Cl.
CPC .......... *A61M 1/3626* (2013.01); *A61M 1/282* (2014.02); *A61M 2205/18* (2013.01)

(58) Field of Classification Search
CPC ................ A61M 1/3626; A61M 1/282; A61M 2205/18; A61M 1/15; A61M 1/152; A61M 1/154; A61M 1/1601; A61M 1/1603; A61M 2205/33; G01R 27/26; G01R 27/2605; G01D 5/24; B01D 61/32
USPC ........................................ 324/658, 686, 690
See application file for complete search history.

(56) References Cited

U.S. PATENT DOCUMENTS

| | | |
|---|---|---|
| 3,602,222 A | 8/1971 | Herndon |
| 3,608,729 A | 9/1971 | Haselden |
| 3,669,878 A | 6/1972 | Marantz |
| 3,669,880 A | 6/1972 | Marantz |
| 3,730,183 A | 5/1973 | Goldsmith |
| 3,754,867 A | 8/1973 | Guenther |
| 3,850,835 A | 11/1974 | Marantz |
| 3,884,808 A | 5/1975 | Scott |
| 3,989,622 A | 11/1976 | Marantz |
| 3,989,625 A | 11/1976 | Mason |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |

(Continued)

FOREIGN PATENT DOCUMENTS

| | | |
|---|---|---|
| CN | 1643368 A | 7/2005 |
| CN | 101193667 | 6/2008 |

(Continued)

OTHER PUBLICATIONS

Gruden, English Translation of Patent Document EP 2,871,468A1, published May 2015. (Year: 2015).*

(Continued)

*Primary Examiner* — Joseph W Drodge
(74) *Attorney, Agent, or Firm* — Hahn & Associates (57) ABSTRACT

Systems, devices, and methods are provided for sensing gas bubbles within a liquid flow line, such as within a medical device. The systems, devices, and methods can measure a change in capacitance across a pair of conductive plates to calculate a volume of gas in a flow line. If a calculated volume of gas exceeds an established threshold, an alert can be sent and/or changes made to operation of the device.

19 Claims, 6 Drawing Sheets

(56) References Cited

U.S. PATENT DOCUMENTS

| | | |
|---|---|---|
| 4,581,141 A | 4/1986 | Ash |
| 4,650,587 A | 3/1987 | Polak |
| 4,661,246 A | 4/1987 | Ash |
| 4,678,408 A | 7/1987 | Mason |
| 4,685,903 A | 8/1987 | Cable |
| 4,747,822 A | 5/1988 | Peabody |
| 4,750,494 A | 6/1988 | King |
| 4,772,560 A | 9/1988 | Attar |
| 4,799,493 A | 1/1989 | DuFault |
| 4,826,663 A | 5/1989 | Alberti |
| 4,828,693 A | 5/1989 | Lindsay |
| 4,976,683 A | 12/1990 | Gauthier |
| 5,032,265 A | 7/1991 | Jha |
| 5,080,653 A | 1/1992 | Voss |
| 5,091,642 A | 2/1992 | Chow |
| 5,092,886 A | 3/1992 | Dobos-Hardy |
| 5,097,122 A | 3/1992 | Colman |
| 5,127,404 A | 7/1992 | Wyborny |
| 5,141,493 A | 8/1992 | Jacobsen |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,364,593 A | 11/1994 | Mihaylov |
| 5,415,838 A | 5/1995 | Rieger |
| 5,468,388 A | 11/1995 | Goddard |
| 5,507,723 A | 4/1996 | Keshaviah |
| 5,643,201 A | 7/1997 | Peabody |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,819,007 A | 10/1998 | Elghazzawi |
| 5,902,336 A | 5/1999 | Mishkin |
| 5,944,684 A | 8/1999 | Roberts |
| 5,987,352 A | 11/1999 | Klein |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,645,191 B1 | 11/2003 | Knerr |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,207,946 B2 | 4/2007 | Sirokman |
| 7,208,092 B2 | 4/2007 | Micheli |
| 7,276,042 B2 | 10/2007 | Polaschegg |
| 7,399,289 B2 | 7/2008 | Gelfand |
| 7,404,799 B1 | 7/2008 | Koh |
| 7,500,958 B2 | 3/2009 | Asbrink |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,775,986 B2 | 8/2010 | Roeher |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,202,503 B2 | 2/2012 | Putnam |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 9,907,897 B2 | 3/2018 | Burbank |
| 2001/0048637 A1 | 12/2001 | Weigl |
| 2002/0016550 A1 | 2/2002 | Sweeney |
| 2002/0042561 A1 | 4/2002 | Schulman |
| 2002/0112609 A1 | 8/2002 | Wong |
| 2002/0145122 A1* | 10/2002 | Duchon ............ A61M 1/3626 250/574 |
| 2003/0028089 A1 | 4/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |

(56) References Cited

U.S. PATENT DOCUMENTS

| | | |
|---|---|---|
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0031972 A1 | 2/2007 | Attar |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0222992 A1 | 9/2007 | Oda |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200865 A1* | 8/2008 | Bedingfield ............ A61M 1/28 604/29 |
| 2008/0200866 A1 | 8/2008 | Prisco |
| 2008/0215247 A1 | 9/2008 | Tonelli |
| 2008/0233008 A1 | 9/2008 | Sarkisov |
| 2008/0253427 A1 | 10/2008 | Kamen |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0149776 A1 | 6/2009 | Adams |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2009/0319204 A1* | 12/2009 | Brown ................ G01F 1/712 702/47 |
| 2010/0004588 A1 | 1/2010 | Yeh |
| 2010/0010425 A1 | 1/2010 | Yu |
| 2010/0010429 A1 | 1/2010 | Childers |
| 2010/0042035 A1 | 2/2010 | Moissl |
| 2010/0061892 A1 | 3/2010 | Flaim |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0092896 A1* | 4/2011 | Kuebler ................ A61M 1/74 604/30 |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Soykan |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Bo Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | QiAn |
| 2013/0168316 A1 | 7/2013 | Noguchi |
| 2013/0186759 A1 | 7/2013 | Lin |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |

(56) References Cited

U.S. PATENT DOCUMENTS

| | | |
|---|---|---|
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0276100 A1 | 9/2014 | Satterfield |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0023467 A1 | 2/2016 | Smith |
| 2016/0143774 A1 | 5/2016 | Burnett |
| 2016/0206801 A1 | 7/2016 | Gerber |
| 2016/0331884 A1 | 11/2016 | Sigg |
| 2018/0043080 A1 | 2/2018 | Gerber |

FOREIGN PATENT DOCUMENTS

| | | | | |
|---|---|---|---|---|
| CN | 101300476 A | 11/2008 | | |
| CN | 101400997 | 1/2009 | | |
| CN | 101482572 | 7/2009 | | |
| CN | 101726465 | 6/2010 | | |
| CN | 202048893 | 3/2011 | | |
| CN | 103037917 | 4/2013 | | |
| CN | 103180712 | 6/2013 | | |
| CN | 103439230 A | 9/2013 | | |
| CN | 103339503 | 10/2013 | | |
| CN | 103803479 | 5/2014 | | |
| CN | 10394587 | 7/2014 | | |
| CN | 103901025 | 7/2014 | | |
| CN | 104685342 | 6/2015 | | |
| CN | 104833635 A | 8/2015 | | |
| CN | 105008893 B | 10/2015 | | |
| CN | 105115952 | 12/2015 | | |
| CN | 105928939 | 7/2016 | | |
| CN | 106124491 | 11/2016 | | |
| CN | 101644667 | 2/2020 | | |
| DE | 3224823 | 1/1984 | | |
| EA | 1514562 | 4/2009 | | |
| EP | 0266795 A2 | 11/1987 | | |
| EP | 0402505 | 12/1990 | | |
| EP | 0272414 | 10/1991 | | |
| EP | 0330892 | 7/1994 | | |
| EP | 1175238 | 11/2000 | | |
| EP | 1085295 | 11/2001 | | |
| EP | 1281351 | 2/2003 | | |
| EP | 2308526 | 10/2003 | | |
| EP | 1523347 | 1/2004 | | |
| EP | 1523350 | 1/2004 | | |
| EP | 0906768 B1 | 2/2004 | | |
| EP | 1691863 | 4/2005 | | |
| EP | 1762263 A1 * | 3/2007 | ............. | A61M 5/36 |
| EP | 2116269 | 2/2008 | | |
| EP | 1450879 | 10/2008 | | |
| EP | 2219703 | 5/2009 | | |
| EP | 1592494 B1 | 6/2009 | | |
| EP | 2398529 | 11/2010 | | |
| EP | 2575827 A2 | 12/2010 | | |
| EP | 2100553 | 8/2011 | | |
| EP | 2576453 A2 | 12/2011 | | |
| EP | 2701580 | 11/2012 | | |
| EP | 2701595 | 11/2012 | | |
| EP | 2344220 B1 | 4/2013 | | |
| EP | 1351756 | 7/2013 | | |
| EP | 2190498 | 7/2013 | | |
| EP | 1364666 A1 | 11/2013 | | |
| EP | 2701596 | 3/2014 | | |
| EP | 2871468 A1 * | 5/2015 | ............. | G01N 27/02 |
| EP | 1582226 | 1/2016 | | |
| JP | S55138462 | 10/1980 | | |
| JP | S63-143077 | 11/1987 | | |
| JP | 2002533170 | 10/2002 | | |
| JP | 2002542900 | 12/2002 | | |
| JP | 2003235965 | 8/2003 | | |
| JP | 2005-533573 | 11/2005 | | |
| JP | 5-9464 | 10/2012 | | |
| WO | 19950038839 | 2/1995 | | |
| WO | WO 1998054563 | 12/1998 | | |
| WO | WO1999006082 | 2/1999 | | |
| WO | 9937342 | 7/1999 | | |
| WO | PCT1124599 | 5/2000 | | |
| WO | 0057935 | 10/2000 | | |
| WO | 2000066197 | 11/2000 | | |
| WO | 200170307 A1 | 9/2001 | | |
| WO | 2001085295 A2 | 9/2001 | | |
| WO | 2002013691 | 2/2002 | | |
| WO | WO 20020053211 | 7/2002 | | |
| WO | 2003043677 A2 | 5/2003 | | |
| WO | 2003043680 | 5/2003 | | |
| WO | 2003051422 A2 | 6/2003 | | |
| WO | 2004008826 | 1/2004 | | |
| WO | 2004009156 | 1/2004 | | |
| WO | 2004009158 | 1/2004 | | |
| WO | 2004030716 A2 | 4/2004 | | |
| WO | 2004030717 A2 | 4/2004 | | |
| WO | 20044064616 A2 | 8/2004 | | |
| WO | 2005033701 | 4/2005 | | |
| WO | 2005061026 | 7/2005 | | |
| WO | 2005123230 A2 | 12/2005 | | |
| WO | 2006011009 | 2/2006 | | |
| WO | 2006017446 | 2/2006 | | |
| WO | 2007038347 | 4/2007 | | |
| WO | 2007089855 A2 | 8/2007 | | |
| WO | 20070115321 | 10/2007 | | |
| WO | WO2009094035 A1 | 1/2008 | | |
| WO | 2008037410 | 4/2008 | | |
| WO | 2009026603 | 12/2008 | | |
| WO | 2009024566 | 2/2009 | | |
| WO | WO2009015882 A2 * | 2/2009 | .......... | A61M 1/1656 |
| WO | 2009061608 | 5/2009 | | |
| WO | 2009094184 | 7/2009 | | |
| WO | 2009157877 A1 | 12/2009 | | |
| WO | 2009157878 A1 | 12/2009 | | |
| WO | WO2009154955 A2 | 12/2009 | | |
| WO | WO 20090154955 | 12/2009 | | |
| WO | WO 20100002830 | 1/2010 | | |
| WO | 2010024963 | 3/2010 | | |
| WO | 2010028860 | 3/2010 | | |
| WO | 2010033314 | 3/2010 | | |
| WO | 2010033699 | 3/2010 | | |
| WO | 2010077851 | 7/2010 | | |
| WO | 2010096659 | 10/2010 | | |
| WO | 2010121820 | 10/2010 | | |
| WO | 2011025705 A1 | 3/2011 | | |
| WO | 2011026645 | 3/2011 | | |
| WO | WO2013022760 A1 | 8/2011 | | |
| WO | WO 2011/132046 | 10/2011 | | |
| WO | 2011137693 | 11/2011 | | |
| WO | WO2011161056 | 12/2011 | | |
| WO | 2012042323 | 4/2012 | | |
| WO | 2012050781 | 4/2012 | | |
| WO | 2012051996 | 4/2012 | | |
| WO | 2012073420 | 7/2012 | | |
| WO | WO 2012/129501 | 9/2012 | | |
| WO | 2012148781 | 11/2012 | | |
| WO | 2012148784 | 11/2012 | | |
| WO | 2012148786 | 11/2012 | | |
| WO | 2012148787 A1 | 11/2012 | | |
| WO | 2012148789 | 11/2012 | | |
| WO | 2012162515 A2 | 11/2012 | | |

(56) References Cited

FOREIGN PATENT DOCUMENTS

| WO | WO2012148788 A1 | 11/2012 |
|---|---|---|
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2014121161 | 8/2014 |
| WO | WO 20140121169 | 8/2014 |
| WO | WO2015081221 A1 | 6/2015 |
| WO | WO 20150130205 | 9/2015 |
| WO | WO 20150159280 | 10/2015 |
| WO | WO 20160080883 | 5/2016 |
| WO | WO 20170034452 | 1/2017 |
| WO | WO 2017/176687 | 10/2017 |
| WO | WO 2017/176701 | 10/2017 |

OTHER PUBLICATIONS

English Translation of Remde patent publication EP1762263A1, published Mar. 2007. (Year: 2007).*
English Translation of Maierhofer et al. patent publication WO2009015882A2, published Feb. 2009. (Year: 2009).*
Brynda, et. al., The detection of toman 2-microglcbuiin by grating coupler immunosensor with three dimensional antibody networks. Biosensors & Bioelectronics, 1999, 363-368, 14(4).
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Zhong, et. al., Miniature urea sensor based on H(+)-ion sensitive field effect transistor and its application in clinical analysis, Chin. J. Biotechnol., 1992, 57-65. 8(1).
PCT/US2012/034331, International Search Report and Written Opinion dated Jul. 9, 2012.
Roberts M, The regenerative dialysis (REDY) sorbent system. Nephrology, 1998, 275-278:4.
Hemametrics, Crit-Line Hematocrit Accuracy, 2003, 1-5, vol. 1, Tech Note No. 11 (Rev. D).
Weissman, S., et al., Hydroxyurea-induced hepatitis in human immunodeficiency virus-positive patients. Clin. Infec. Dis, (Jul. 29, 1999): 223-224.
PCT/US2012/034334, International Search Report, dated Jul. 6, 2012.
PCT/US2012/034335, International Search Report, dated Sep. 5, 2012.
PCT/US/2012/034327, International Search Report, dated Aug. 13, 2013.
PCT/US/2012/034329, International Search Report, dated Dec. 3, 2012.
Foley, et al., Long Interdialytic Interval and Martiality among Patients Receiving Hemodialysis, N Engl Jrnl Med. 2011:365(12):1099-1107.
PCT International Search Report from International Application No. PCT/US2014/067650, dated Mar. 9, 2015.
Wang, Fundamentals of intrathoracic impedance monitoring in heart failure, Am. J. Cardiology, 2007, 3G-10G: Suppl.
PCT/US2014/067650 International Search Report Written Opinion dated Mar. 9, 2015.
Bleyer, et al, Kidney International. Jun. 2006; 69(12):2268-2273.
Bleyer, et. al., Sudden and cardiac death rated in hemodialysis patients, Kidney International. 1999, 1553-1559: 55.
PCT/US2012/034335, International Preliminary Report on Patentability, dated Oct. 29, 2013.
PCT/US2012/034303, Internationa Search Report, dated Jul. 6, 2013.
PCT/US2012/034332, International Preliminary Report on Patentability, dated Oct. 29, 2013.
PCT/US2012/034333, International Report on Patentabilty, dated Oct. 29, 2013.
PCT/US2012/034333, International Search Report, dated Aug. 29, 2012.
PCT/US2012/034327, International Preliminary Report on Patentability, dated Oct. 29, 2013.
PCT/US2012/034330, International Preliminary Report on Patentability, dated Oct. 29, 2013.
Culleton, BF et al. Effect of Frequent Nocturnal Hemodialysis vs Conventional Hemodialysis on Left Ventricular Mass and Quality of Liife. 2007 Journal of the American Medical Association 298 (11), 1291-1299.
Redfield, et. al, Restoration of renal response to atrial natriuretic factor in experimental low-output heart failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
PCT/US2012/034329, International Preliminary Report on Patentability, dated Oct. 29, 2013.
Lima, et. al., An electrochemical sensor based on nanostructure sensor based on nanostructure hollsndite-type manganese oxide for detection of potassium ion, Sensors, Aug. 24, 2009, 6613-8625, 9.
MacLean, et, al., Effects of hindlimb contraction on pressor and muscle interstitial metabolite responses in the cat, J. App. Physiol., 1998, 1583-1592, 85(4).
International Search Report and Written Opinion dated May 19, 2014.
PCT/US2014/014357 International Search Report and Written Opinion dated May 19, 2014.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. P 280: R48-R55, Jan. 1, 2001.
Overgaard et. al., Relations between excitability and contractility in rate soleusmuscle: role of the NA+-K+ pump and NA+-K-S gradients. Journal of Physiology, 1999, 215-225, 518(1).
Zoccali, Pulmonary Congestion Predicts Cardiac Events and Mortality in ESRD, Clinical Epidemiology, J. Am Soc Nephrol 24:639-646, 2013.
Coast, et al. 1990, An approach to Cardiac Arrhythmia analysis Using Hidden Markov Models, IEEE Transactions On Biomedical Engineering. 1990, 37(9):826-835.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report dated May 26, 2015.
Genovesi, et al., Nephrology, Dialysis, Transplantation 2009; 24(8):2529-2536.

(56) References Cited

OTHER PUBLICATIONS

Secemsky, et al., High prevalence of cardiac autonomic dysfunction and T-wave alternans in dialysis patients. Heart Rhythm, Apr. 2011, 592-598 : vol. 8, No. 4.
Wei, et al., Fullerene-cryptand coated piezoelectric crystal urea sensor based on urease, Analytica Chimica Acta, 2001,77-85:437.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
Leifer et al., A Study on the Temperature Variation of Rise Velocity for Large Clean Bubbles, J. Atmospheric & Oceanic Tech., vol. 17, pp. 1392-1402, Oct. 2000.
Talaia, Terminal Velocity of a Bubble Rise in a Liquid Column, World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
PCT/US2012/034332, International Search Report, dated Jul. 5, 2012.
Siegenthaler, et al., Pulmonary Fluid status monitoring with intrathoracic impedance, Journal of Clinical Monitoring and Computing, 24:449-451, published Jan. 12, 2011.
John Wm Agar: Review Understanding sorbent dialysis systems, Nephrology, vol. 15, No. 4, Jun. 1, 2010, pp. 406-411.
European Office Action in Application 12717020.7 dated Sep. 14, 2016.
Lakerveld et al, Primary prevention of diabetes mellitus type 2 and cardiovascular diseases using a cognitive behavior program aimed at lifestyle changes at risk: Design of a randomized controlled trial, 2008, BMC Endocrine Disorders, 8(6): 1-19.
Gordhandas et al, Real-Time Extraction and Analysis of Key Morphological Features in the Electrocardiogram, for Data Compression and Clinical Decision Support, 2004, Computional Physiology, pp. 15-18.
European Office Action in Application 12717020.7 dated Dec. 11, 2015.
PCT/US2012/034331 International Preliminary Report on Patentability and Written Opinion dated Oct. 29, 2013.
Office Action in Chinese Application No. 201280020932.1 dated Jan. 7, 2015.
Office Action in Chinese Application No. 201280020932.1 dated Apr. 3, 2015.
PCT/US2012/034330, International Search Report and Written Opinion dated Aug. 28, 2012.
Office Action in Japanese Application No. 2014-508434 dated Nov. 16, 2015.
Office Action in Japanese Application No. 2014-508434 dated Dec. 8, 2014.
Office Action in Japanese Application No. 2014-508434 dated Nov. 4, 2016.
Office Action in European Application No. 12717019.9 dated Feb. 16, 2017.
Office Action in Chinese Application No. 201510511657.9 dated May 10, 2017.
PCT/US2014/065201 International Preliminary Report on Patentability dated May 19, 2016.
Office Action in European Application No. EP 12717021.5 dated Feb. 3, 2017.
Office Action in Chinese Application No. 201510593695.3 dated Jul. 12, 2017.
Office Action in European Application No. EP 12719170.8 dated Jan. 14, 2015.
Office Action in Japanese Application No. JP 2014-508437 dated Dec. 8, 2014.

Nedelkov, et. al., Design of buffer exchange surfaces and sensor chips for biosensor chip mass spectrometry, Proteomics, 2002, 441-446, 2(4).
European Search Report App 14865374.4, dated Jun. 12, 2017.
European Search Report for Application No. 14865128.4 dated Jun. 20, 2017.
Green et al., Sudden Cardiac Death in Hemodialysis Patients: an In-Depth Review, Am J Kidney Dis 57(6)921:929; published Apr. 18, 2011.
Rajan et al. Generalized Feature Extraction for Time-Varying Autoregressive Models, IEEE Transactions Signal Processing vol. 44, No. 10; published Oct. 1, 1996.
AU Examiners Report for Application No. 2017246829, dated Jan. 9, 2021.
Castellanos, et al, Clinical Relevance of Intraperitoneal Pressure in Peritoneal Dialysis Patients, Perit Dial Int. Sep. Oct. 2017;37(5):562-567. doi: 10.3747/pdi.2016.00267. Epub Jul. 11, 2017.
Chinese Office Action for App. No. 201710778666.3, dated Feb. 25, 2020.
Chinese Office Action for App. No. 201710778666.3, dated Jul. 15, 2020.
Chinese Office Action for App. No. 201710778666.3, dated Nov. 20, 2020.
Chinese Office Action for App. No. 201710779349.3, dated Jun. 1, 2020.
Chinese Office Action for App. No. 201710779964.4, dated Apr. 14, 2020.
Chinese Office Action for App. No. 201710779964.4, dated Aug. 26, 2020.
Chinese Office Action for App. No. 2019071601874110, dated Jul. 19, 2019.
Chinese Office Action in App. No. 201480059332.5, dated Mar. 30, 2018.
Dejardin, et al, Intraperitoneal pressure in PD patients: relationship to intraperitoneal volume, body size and PD-related complications, Nephrol Dial Transplant. May 2007;22(5):1437-44.
European Office Action for App. No. 17190053.3, dated Sep. 18, 2019.
European Search For App. No. 17190081.4, dated Feb. 5, 2021.
European Search Report for App. No. 17185636.2, dated Mar. 27, 2018.
European Search Report for App. No. 14859115.9, dated Jan. 5, 2018.
European Search Report for App. No. 17185636.2 dated Jan. 10, 2018.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
European Search Report for App. No. 17190053.3, dated Jan. 2, 2018.
European Search Report for App. No. 17190066.5, dated Jan. 16, 2018.
European Search Report for App. No. 17190081.4, dated Sep. 16, 2019.
European Search Report for App. No. 17190084.8, dated Feb. 9, 2018.
Henderson, et al., "Online Preparation of Sterile Pyrogen-Free Electrolyte Solution," Trans. Am. Soc. Artif. Intern.Organs, 1978 pp. 465-467.
Indian OA of Nov. 21, 2019 in 2981/KOLNP/2013.
Indian Office Action for Application 201714030219, dated May 31, 2021.
International Preliminary Report on Patentability for App. No. PCT/US2019/019334, dated Jun. 12, 2019.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
Office Action for Chinese Application No. 201710779349.3, dated Oct. 9, 2019.

(56) References Cited

OTHER PUBLICATIONS

Office Action for European App. No. 17190066.5, dated Mar. 7, 2019.
Office Action in Chinese App. No. 201710778666.3 dated Sep. 19, 2019.
PCT/US2016/058579 International Search Report dated Jan. 31, 2017.
PCT/US2016/058579 Written Opinion dated Jan. 31, 2017.
PCT/US2017/025868 International Search Report dated Jun. 29, 2017.
PCT/US2017/025868 Written Opinion dated Jun. 29, 2017.
PCT/US2017/030377 International Search Report dated Sep. 1, 2017.
PCT/US2017/030377 Written Opinion dated Sep. 1, 2017.
PCTUS20170146199 ISR and written opinion, dated Feb. 19, 2018.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Schmitt, et al, "Colorimetric Gas Sensing with Enhanced Sensitivity," Procedia Engineering, vol. 168, Sep. 3, 2016, pp. 1237-1240.
Wollenstein, et al, "Colormetric gas sensors for the detection of ammonia, nitrogen dioxide, and carbon monoxide: current status and research trends", Sensor and Test Conference 2011, Jan. 2, 2011, pp. 562-567.
Written Opinion in Dutch App. No. 2018577, dated Nov. 2, 2017.
"Resources, environment and sustainable development of agriculture," edited by Liu Zhaopu, China Agricultural Science and Technology Press, pp. 209-211, Aug. 31, 1994.
"Rural Medical and Health Handbook," written by Shanghai "Rrural Medical and Health Handbook Writing team, Shanghai Science and Technology Press, Jun. 1968, p. 435.
"Surface water environmental quality standard non-ionic ammonia conversion method," Teng Enjiang, et al, "China Environental Monitoring," vol. 11, No. 4, pp. 7-9, Dec. 31, 1995.

\* cited by examiner

GAS BUBBLE SENSOR

FIELD

The disclosure relates to systems, devices, and methods for sensing the presence of gas bubbles in a liquid flow line. The flow line may be for administration of a medical fluid, or any other passage in which liquid flow is regulated.

BACKGROUND

Gas intrusion within the liquid is sometimes minimized in systems, methods, and devices that involve the transportation of liquid. For example, devices that administer fluids to patients should not carry air or other gas bubbles beyond a certain size because such bubbles could harm the patient. Devices that involve admixture of different components to generate a desired result should be designed to ensure that the mixing process does not introduce too much extraneous gas into the resulting mixture. Some devices include optical sensors to detect gas bubbles in flow lines. However, the known sensors are dependent on the optical properties of the lines and the relative opacity of the liquid relative to possible gasses in order to consistently function. Hence, a need exists for a gas bubble sensor that can accurately and precisely determine the presence of gas bubbles in a liquid flow line. A related need is to identify bubbles having a size that could harm a patient. There is a related need for systems and methods that are not are dependent on the optical properties of the lines and the relative opacity of the liquid relative to possible gasses.

SUMMARY OF THE INVENTION

The first aspect relates to a gas bubble sensor. In any embodiment, the gas bubble sensor can include first and second conductive plates forming a capacitor with a capacitance that varies with the dielectric properties of a liquid flow line within a dialysis system; a capacitance sensor measuring the capacitance between the first conductive plate and the second conductive plate; and a control system programmed to determine a presence of one or more gas bubbles within the liquid flow line based on the capacitance between the first conductive plate and the second conductive plate.

In any embodiment, the dialysis system can be a peritoneal dialysis system.

In any embodiment, the gas bubble detector can be in a peritoneal dialysis cycler. In any embodiment, the gas bubble can be detected based on the dielectric properties of peritoneal dialysis fluid transported by the flow line and by the dielectric properties of air.

In any embodiment, the first conductive plate and the second conductive plate can be made of a conductive metal alloy.

The features disclosed as being part of the first aspect can be in the first aspect either alone or in combination, or follow any arrangement or permutation of any one or more of the described elements. Similarly, any features disclosed as being part of the first aspect can be in a second or third aspect described below, either alone or in combination, or follow any arrangement or permutation of any one or more of the described elements.

The second aspect relates to a dialysis system. In any embodiment, the dialysis system includes a first liquid flow line and a gas bubble detector. The gas bubble detector, in turn, includes first and second conductive plates forming a capacitor with a capacitance that varies with the dielectric properties of the liquid flow line, and a capacitance sensor measuring the capacitance between the first conductive plate and the second conductive plate.

In any embodiment, the dialysis system can also include a control system programmed to determine a presence of one or more gas bubbles within the liquid flow line based on the capacitance between the first conductive plate and the second conductive plate.

In any embodiment, the control system can be programmed to provide an alert when a volume of gas bubbles detected exceeds a predetermined volume.

In any embodiment, the control system can be programmed to automatically modify operation of the dialysis system when a volume of gas bubbles detected exceeds a predetermined volume.

In any embodiment, the dialysis system can be a peritoneal dialysis system.

In any embodiment, the gas bubble detector can be positioned in a cycler of the peritoneal dialysis system.

In any embodiment, the first liquid flow line can be within a first dialysis cassette.

In any embodiment, the dialysis system can include a second dialysis cassette having a second liquid flow line, and the first and second conductive plates can be positioned on components of the system outside the first and second dialysis cassettes. When the first cassette is installed within the dialysis system for use during therapy, the capacitance between the first and second plates varies with the dielectric properties of the first liquid flow line. When the first cassette is removed and the second cassette is installed within the dialysis system for use during therapy, the capacitance between the first and second plates varies with the dielectric properties of the second liquid flow line.

In any embodiment, the dialysis system can include a housing with a receiving slot for the first or second dialysis cassette and a hinged door over the receiving slot. The first conductive plate can be positioned in the housing adjacent the receiving slot and the second conductive plate can be positioned in the hinged door.

In any embodiment, the dialysis system can include a housing with a receiving slot and a slidable tray for the first or second dialysis cassette. The first conductive plate can be positioned inside the receiving slot and the second conductive plate can be positioned on the slideable tray.

The features disclosed as being part of the second aspect can be in the second aspect either alone or in combination, or follow any arrangement or permutation of any one or more of the described elements. Similarly, any features disclosed as being part of the second aspect can be in the first or third aspect described above and below, either alone or in combination, or follow any arrangement or permutation of any one or more of the described elements.

The third aspect relates to a method using a dialysis system. In any embodiment, the dialysis system includes a first liquid flow line and a gas bubble detector. The gas bubble detector, in turn, includes first and second conductive plates forming a capacitor with a capacitance that varies with the dielectric properties of the liquid flow line, and a capacitance sensor measuring the capacitance between the first conductive plate and the second conductive plate. In any embodiment, the method includes the steps of: detecting a capacitance between the first conductive plate and the second conductive plate during dialysis treatment; and determining the presence of one or more gas bubbles in the first liquid flow line based on the detected capacitance.

In any embodiment, the step of determining the presence of one or more gas bubbles in the first liquid flow line is performed by a control system of the dialysis system.

In any embodiment, the method further includes the step of providing an alert if the detected capacitance drops below a predetermined value.

In any embodiment, the method further includes the step of stopping therapy if the detected capacitance drops below a predetermined value.

In any embodiment, the step of modifying operation of the dialysis system to divert liquid flow away from the first liquid flow line if the detect capacitance drops below a predetermined value.

The features disclosed as being part of the third aspect can be in the third aspect either alone or in combination, or follow any arrangement or permutation of any one or more of the described elements. Similarly, any features disclosed as being part of the third aspect can be in the first or second aspect either alone or in combination, or follow any arrangement or permutation of any one or more of the described elements.

DETAILED DESCRIPTION

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

A "capacitor" is an arrangement of elements within an electric circuit that hold an electric charge. Each capacitor includes a pair of conductive plates and has a characteristic capacitance.

The terms "communication," "communicate," "communicating," and the like can refer to the ability to transmit electronic data, instructions, information wirelessly, via direct electrical connection, or any other electrical transmission means between one or more components.

The term "comprising" includes, but is not limited to, whatever follows the word "comprising." Use of the term indicates the listed elements are required or mandatory but that other elements are optional and may be present.

A "conductive metal alloy" is a material that conducts electricity and that includes at least one metal element in its composition. There is no requirement that the alloy be more conductive than its constituent materials, provided the alloy is used as the material for a conductive plate.

A "conductive plate" is any element that acts as a capacitor within a circuit. No particular limits or thresholds to conductance are required for a component to be a "conductive plate," provided the plate acts as a capacitor.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "device," as used herein, refers to any device that can authenticate a user or USB authentication device.

The term "determining" or to "determine" refers to ascertaining a particular state of a component or system.

The term "device" is to be interpreted in the broadest and can include anything made for a particular purpose; a contrivance of any type, particularly a mechanical or electrical component or hardware. Some examples of devices can include a medical device such as a dialysis machine, laptop, computer, computer peripherals of any type, computer terminals, portable devices, smart phones, and smart watches.

A "dialysis system" is a collection of medical devices used to provide dialysis treatment to one or more patients.

A "fluid line" is a passage within a device that is used to transport fluid in one or both directions.

A "gas bubble" is a contiguous volume of gas inside a liquid.

A component is "intrusive" if positioned within a chamber for holding or transporting liquid such that the component will come in physical contact with the liquid.

The term "medical device" refers to a device used to perform medical treatment or diagnosis of any type.

To "measure" is to determine a quantifiable property of a component or system via a sensor.

A system or method is "non-intrusive" if the system or method contains no intrusive components—that is, if every component of the system or used to implement the method is positioned outside of the chambers where liquid is transported and stored so that none of the components come in physical contact with the liquid.

A "peritoneal dialysis system" is a collection of medical devices used to provide peritoneal dialysis treatment to a patient.

The term "peritoneal dialysis fluid" refers to the mixture that is injected into a patient during peritoneal dialysis treatment. When properties of peritoneal dialysis fluid are described herein, such as its dielectric properties and permittivity, they refer to the properties of the fluid before its use in treatment.

The term "programmed" can mean a series of instructions that cause a device or system to perform certain steps.

A "sensor" is a device configured to determine a particular state of a component or system.

Gas Bubble Sensor

Figure 1:
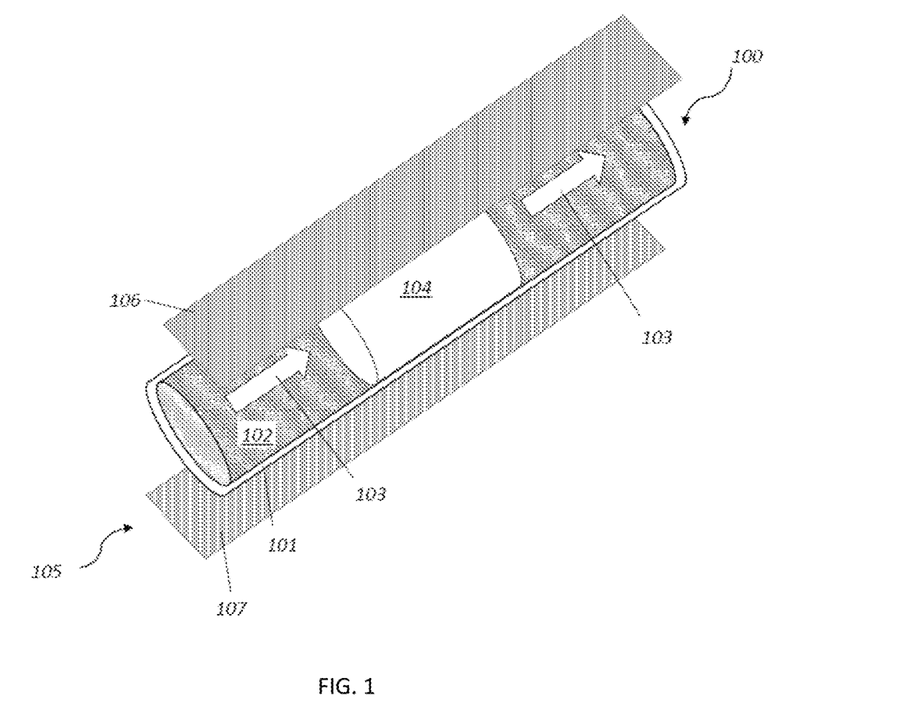
FIG. 1 is a cross-sectional view of a flow line and an adjacent capacitor.

FIG. 1 illustrates a flow line with a gas bubble. As shown, the flow line 100 is comprised of a tube 101 in which a liquid 102 flows. The liquid 102 moves in the flow direction as illustrated by the arrows 103, but the flow may be partially disrupted by the presence of a gas bubble 104 as shown. Depending on the properties of the gas, the liquid, and the flow line (including, for example, the specific gravity of both fluids and the pressure and velocity under which the flow line is kept during operation) the gas bubble 104 may move at a different speed than the liquid, or in some situations may even remain at rest or move in the opposite direction from the liquid flow within the flow line 100.

The shape of the gas bubble 104 is illustrated in FIG. 1 as cylindrical, but the actual shape of a gas bubble within the liquid may also depend on the geometry of the flow line 100 and the physical properties of the fluids. The liquid flow line could, for example, transport a deionized, filtered, or otherwise purified sample of water. As another example, a fluid used for medical treatment, such as dialysis, could be transported by the liquid flow line. A gas bubble could be air intruding from outside the flow line, vapor of the transported liquid itself, or the product of another process of the system. Where two or more components are mixed to produce a liquid that is then carried by the flow line, a gas could be a byproduct of the admixture and then intrude into the flow line.

A capacitor 105 is formed by a pair of conductive plates 106 and 107 adjacent the flow line 100. In this embodiment, the plates 106, 107 are non-intrusive: they are positioned exterior to the tube 101 of the flow line 100 and therefore will not come into physical contact with the liquid 102 or the gas bubble 104. The conductive plates may be made of any material known in the art to carry an electric charge. Conductive metal alloys are often used as the material for these conductive plates, which may include aluminum, copper, silver, tantalum, gold, tin, and others.

Figure 2:
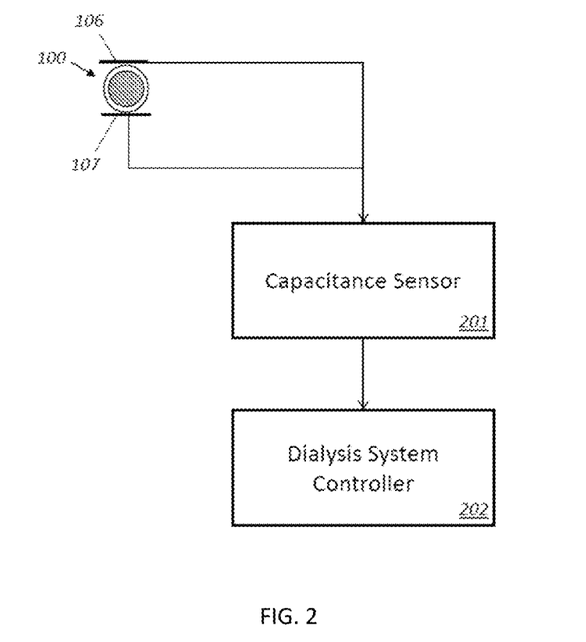
FIG. 2 is a diagram showing components of a gas bubble sensor connected to a flow line and an adjacent capacitor.

As shown in FIG. 2, the conductive plates 106 and 107 are connected to a capacitance sensor 201 which in turn communicates data to a controller 202 for a dialysis system. The capacitance sensor 201 and plates 106, 107 may, in some implementations, be part of the same electrical system which may also provide power to a circuit to allow the capacitor 105 to operate. In some implementations, these components may all be considered integral to the dialysis system for which the controller 202 is also a component.

The position and relative orientation of the plates 106, 107 results in their capacitance depending on the dielectric properties of the flow line 100 and its contents. Particularly, the capacitance will be proportional to the permittivity of the flow line:

$$C \propto \varepsilon_{flow\ line}$$

Furthermore, the permittivity of the flowline is a weighted function of the permittivity of its component parts. That is:

$$\varepsilon_{flow\ line} = \varepsilon_1 * V_1 + \varepsilon_2 * V_2 + \varepsilon_3 * V_3$$

Where each $\varepsilon_n$ and $V_n$ represents the permittivity of a different component present in the flow line and the volume of that component. This allows us to calculate the expected change in the permittivity of the flow line if bubble of volume $V_{bubble}$ having permittivity $\varepsilon_{gas}$ replaces a liquid having permittivity $\varepsilon_{liquid}$. The difference would be as follows:

$$\Delta\varepsilon_{flow\ line} = \varepsilon_{gas} * V_{bubble} - \varepsilon_{liquid} * V_{bubble} = (\varepsilon_{gas} - \varepsilon_{liquid}) * V_{bubble}$$

The change in permittivity of the flow line is therefore directly proportional to the difference between the permittivity of the gas and the permittivity of the liquid, and to the volume of the bubble. Therefore, when liquid in the flow line is replaced by an air bubble, there will be a change in the capacitance of the conductive plates 106, 107 that is proportional to the volume of the air bubble:

$$\Delta C \propto V_{bubble}$$

Monitoring the capacitance of the plates will therefore alert the system to the presence of gas bubbles in the flow line.

A variety of conventional circuit elements may be employed to monitor the capacitance, such as by running a current of known amperage across the capacitor in conjunction with a resistor or inductor. A measured change in the voltage of the circuit is registered as the capacitance. Any conventional capacitance sensor 201 appropriate for use in the dialysis system may be included.

Figure 3:
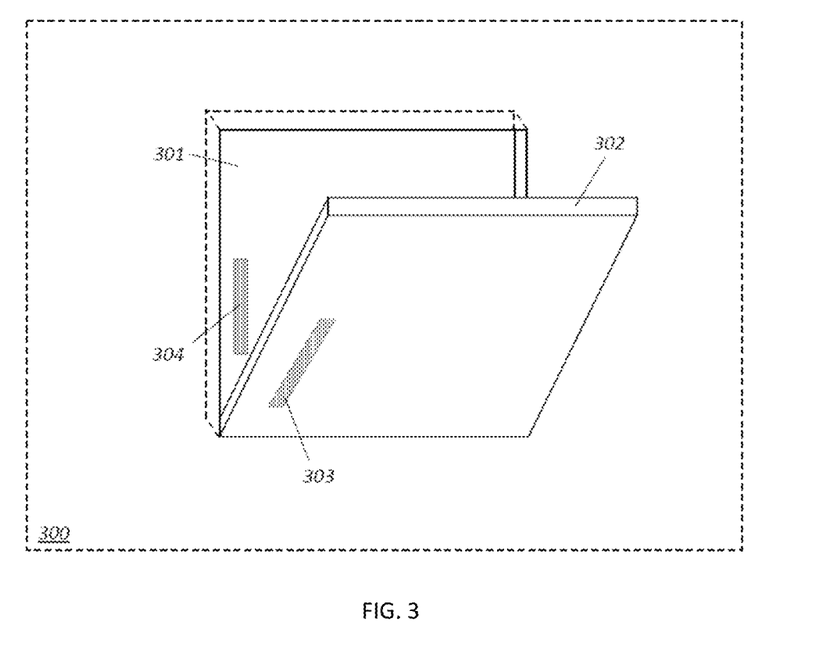
FIG. 3 is a side view of a dialysis system housing for a dialysis cassette in the open position.
Figure 4:
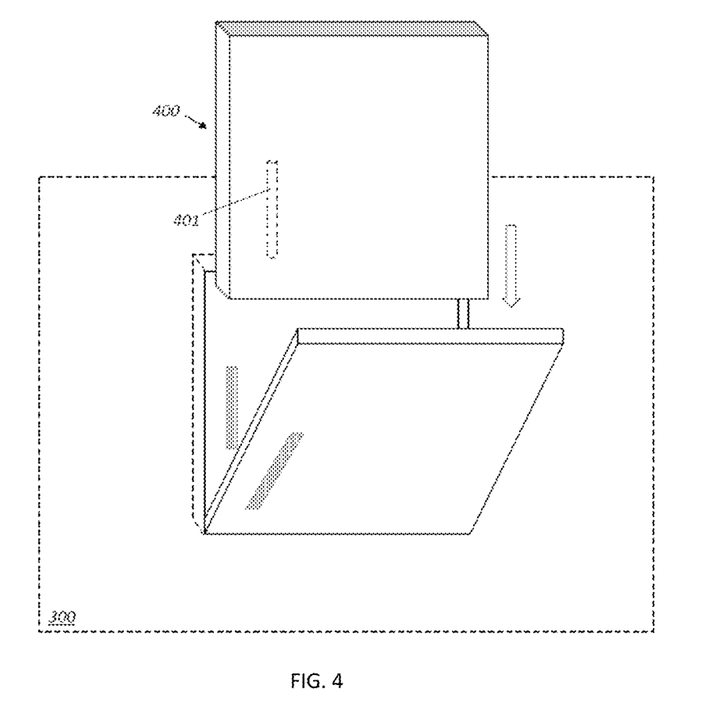
FIG. 4 is a side view of a dialysis cassette being inserted into a dialysis system housing.
Figure 5:
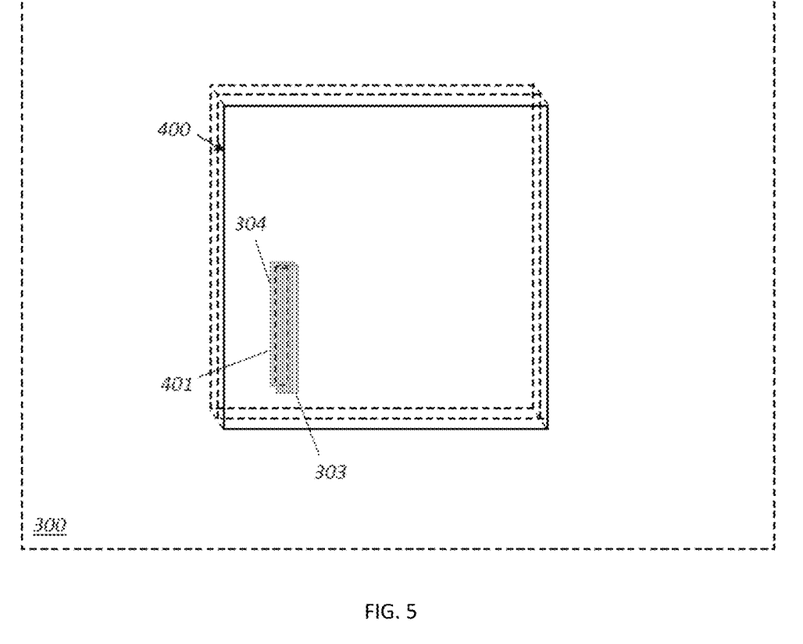
FIG. 5 is a side view of a dialysis system housing holding a dialysis cassette in the closed position.

FIGS. 3-5 illustrate a particular embodiment of a dialysis system with a gas bubble sensor as described herein. FIG. 3 shows a housing 300 for a dialysis cassette, which docks into a recess 301 when deployed therein. A door 302, shown in the open position, covers the recess 301 when closed. A first conductive plate 303 is embedded in the door 302, parallel to the front surface of the door 302 and housing 300. A second conductive plate 304 is embedded in a rear wall of the recess 301, parallel to the first plate 303 and the front surfaces.

FIG. 4 shows a cassette 400 with a flow line 401 embedded therein. The flow line 401 is integral to the cassette 400, which acts as part of a cycling mechanism for dialysis treatment.

Figure 7:
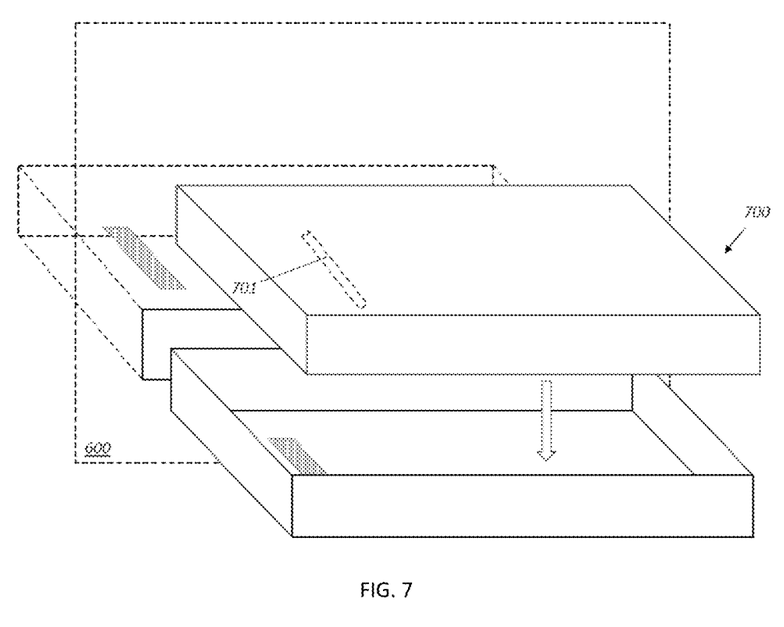
FIG. 7 is a side view of a dialysis cassette being inserted into a dialysis system housing.

FIGS. 4 and 7 illustrate the cassette 400 docking into the recess 301 and the door 302 closing, at which point the conductive plates 303, 304 are each positioned so that an air bubble in the flow line 401 affects their conductance, as described above. In this way, once the cassette 400 is loaded into the housing 300, the gas bubble sensor is also in position to monitor the flow line 401.

As shown in FIGS. 4-7, the conductive plates 303, 304 are embedded in the housing 300 and not the cassette 400. In this embodiment, when one cassette is removed and another cassette having a flow line in a similar location is installed, the flow line in the newly installed cassette can be monitored using the same sensor.

Figure 6:
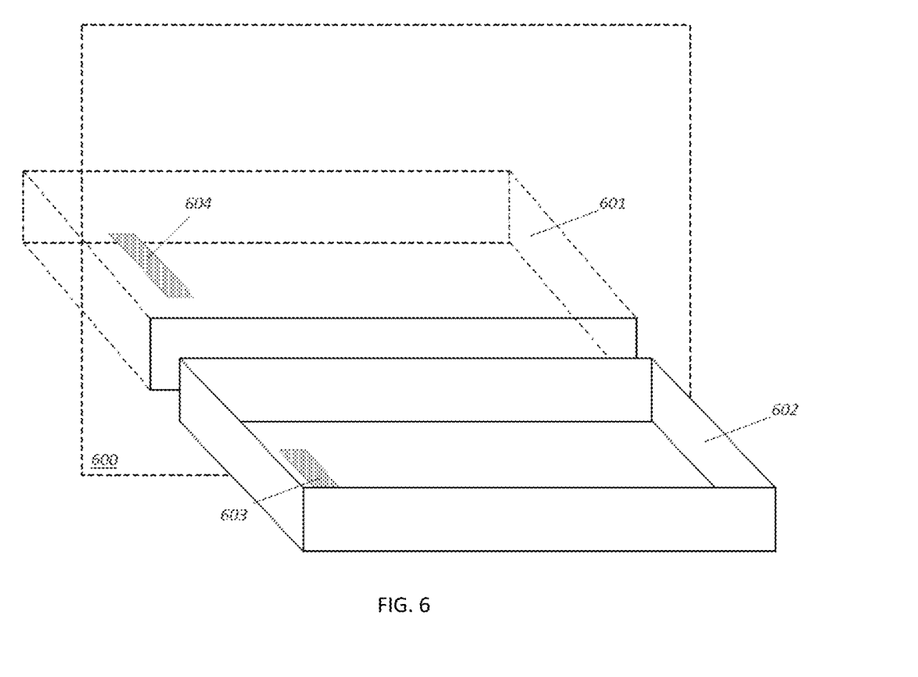
FIG. 6 is a side view of a dialysis system housing for a dialysis cassette in the open position.
Figure 8:
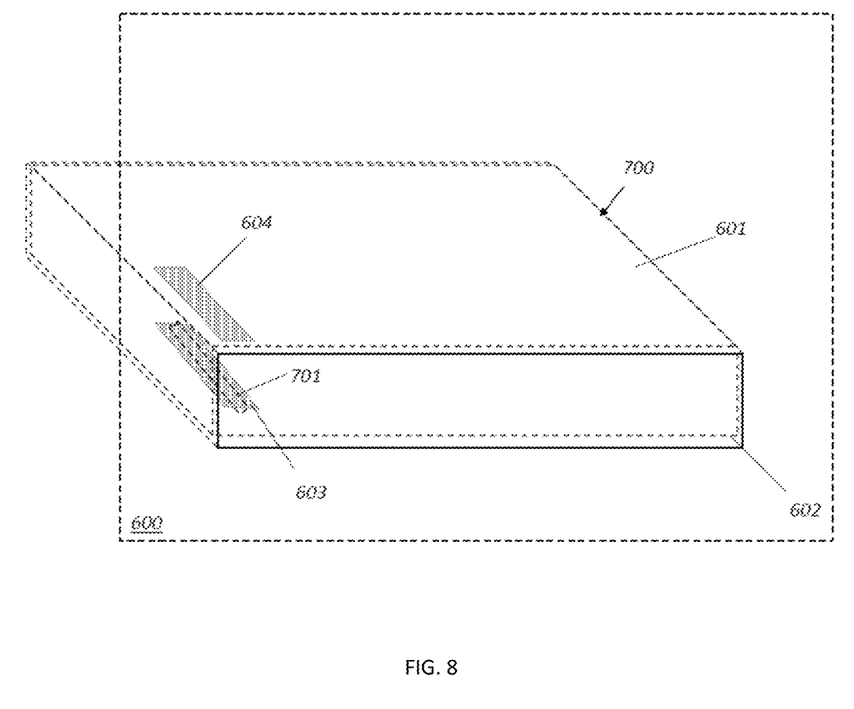
FIG. 8 is a side view of a dialysis system housing holding a dialysis cassette in the closed position.

FIGS. 6-8 illustrate a particular embodiment of a dialysis system with a gas bubble sensor as described herein. FIG. 6 shows a housing 600 for a dialysis cassette, which docks into a recess 601 when deployed therein. A slidable tray 602, shown in the open position, receives the cassette and slides into the recess 601 when closed. A first conductive plate 603 is embedded in the tray 602, parallel to the bottom surface of the tray 602 and recess 601. A second conductive plate 604 is embedded in a top wall of the recess 601, parallel to the first plate 603 and perpendicular to the front surfaces.

FIG. 7 shows a cassette 700 with a flow line 701 embedded therein. The flow line 701 is integral to the cassette 700, which acts as part of a cycling mechanism for dialysis treatment.

FIGS. 7 and 8 illustrate the cassette 700 docking into the tray 602 and the tray sliding into the recess 601, at which point the conductive plates 603, 604 are each positioned so that an air bubble in the flow line 701 affects their conductance, as described above. In this way, once the cassette 700 is loaded into the housing 600, the gas bubble sensor is also in position to monitor the flow line 701.

As shown in FIGS. 6-8, the conductive plates 603, 604 are embedded in the housing 600 and not the cassette 700. In this embodiment, when one cassette is removed and another cassette having a flow line in a similar location is installed, the flow line in the newly installed cassette can be monitored using the same sensor.

Figure 9:
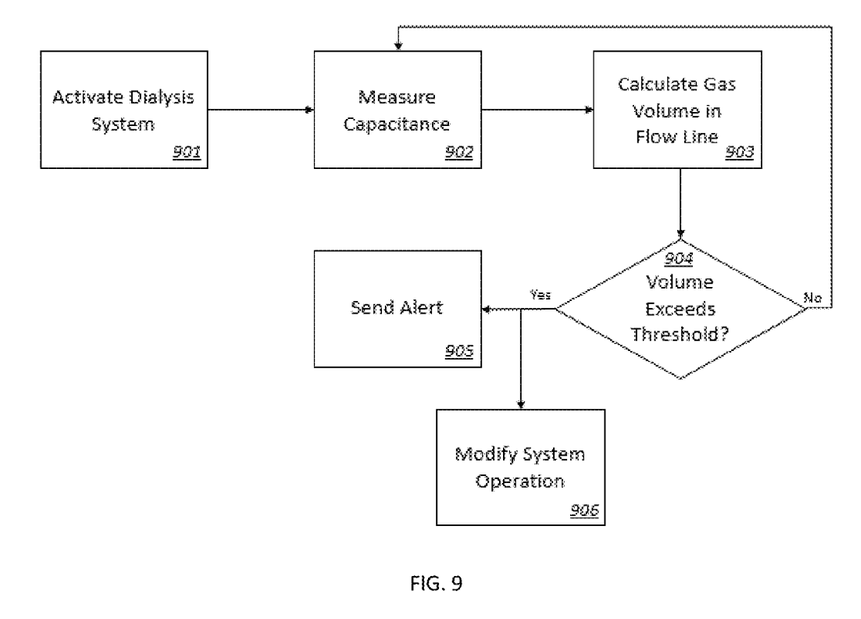
FIG. 9 is a flow chart showing steps for detecting a gas bubble in a flow line of a dialysis system.

FIG. 9 is a flowchart illustrating the steps by which a flow line may be monitored during operation of a dialysis system. In step 901, a dialysis system is activated. System activation may be automatic or manual, triggered through an interface with a dialysis system controller as described above or by connecting and priming one or more components of the system.

When the system is activated, steps 902, 903, and 904 together form a loop for monitoring a flow line within the dialysis system for gas bubbles. In step 902, the capacitance between two conductive plates positioned near the flow line, as described and shown above, is measured. In step 903, the capacitance is then used to calculate a volume of gas in the flow line.

In some embodiments, the process for measuring the capacitance and calculating the gas in the flow line may involve establishing a reference value for the capacitance, which is then compared to each measurement to determine a drop that registers as a gas intrusion. For example, the capacitance of the flow line may be measured when the dialysis system is not activated but the flow line is filled with liquid, so that no gas bubbles will yet be present. The reference value may also be supplied externally to the controller as a predetermined value, or may be generated over time from a statistical sampling taken from measurements while the system is operating.

In step 904, the calculated volume of gas is compared against a threshold, which is based on the safe operation of the device relative to the function of the flow line being monitored. For example, if the flow line provides purified water to an admixture, the resulting fluid may have a different tolerance for gas intrusion than a flow line administering medical fluid to a patient. The threshold may also vary over the course of treatment as the character and use of the fluid in the flow line changes. For example, if the rate of administration of fluid slows, the threshold volume of gas for safe operation of the flow line may likewise change.

As long as the volume of gas does not exceed the threshold, the monitoring process continues from step 902. When the calculated volume does exceed the threshold, one or both of the steps 905 and 906 are taken as shown by the branching arrows in the flowchart of FIG. 8.

In step 905, an alert is sent providing information about the air bubble. The alert may be displayed to a user through an interface of the dialysis system or may be communicated internally within the dialysis system. In some cases, the alert may include a record of the threshold, which may be later be consulted with other records to determine the state of the flow line or the dialysis system.

In step 906, operation of the dialysis system is modified based on the detected air bubble. This may include pausing or halting a therapeutic treatment or providing a user of the dialysis system an opportunity to pause or halt the treatment. This step also may include altering the properties of the flow line, such as changing liquid speed or pressure entering or exiting the flow line. In some embodiments, the flow line might be temporarily disconnected from the system to eject the portion of liquid including the gas volume, then reconnected. This step may also include diverting the system to use a different flow line than the one in which the gas bubble is detected, such as automatically or manually replacing a dialysis cassette or other component including the flow line.

Whether one or both of steps 905 and 906 are taken, and what particular actions are taken in one or both steps, may in some embodiments depend on the particular volume of gas bubble detected. Therefore, while FIG. 8 shows a step with a single threshold, a controller may compare the calculated volume against different thresholds in different system states to determine the correct steps to take based on the measured and calculated data.

Figure 10:
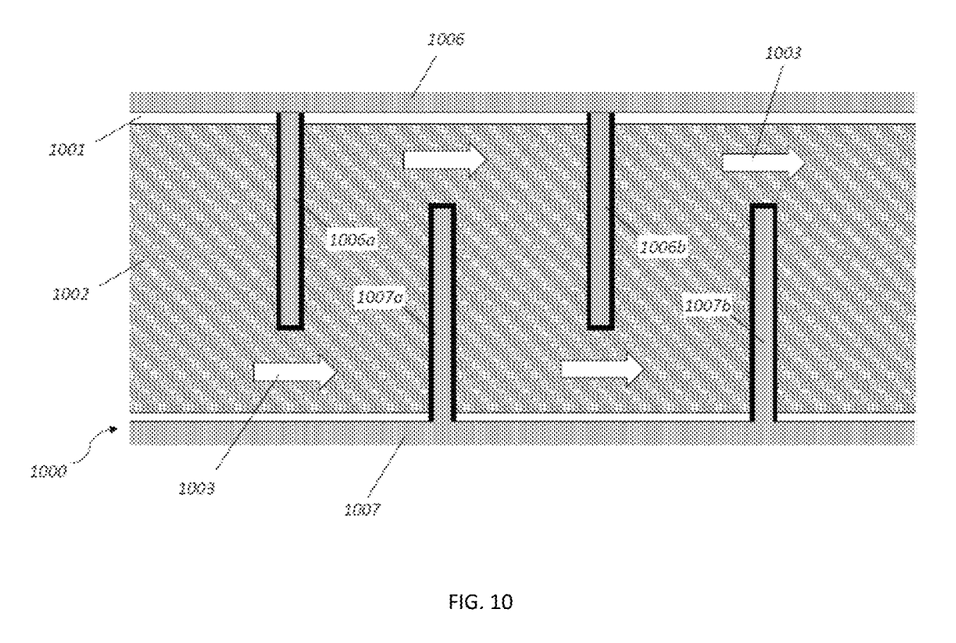
FIG. 10 is a cross-sectional view of a flow line with a comb plates disposed within the fluid flow forming a capacitor.

FIG. 10 shows another embodiment of a system that includes a device for detecting gas bubbles within a flow line. The flow line 1000 includes a tube 1001 in which liquid 1002 flows in the direction shown by the arrows 1003. The capacitor is composed of conductive plates 1006 and 1007, which, in this case, include comb plates 1006a,b and 1007a,b respectively. The comb plates 1006a,b and 1007a,b protrude into tube 1001 and contact the liquid 1002, diverting its flow to go around the plates, and providing additional effective length for the segment of flow line that is under detection by the capacitor.

Each of the conductive plates 1006 and 1007 is in communication with a capacitance sensor as described with respect to FIG. 2, above, or as otherwise described herein, as could any additional configuration of a capacitor in conjunction with a flow line as known in the art.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a device.

I claim:

1. A dialysis system comprising a liquid flow line, a control system, and a gas bubble detector, the gas bubble detector comprising:
    first and second conductive plates forming a capacitor with a capacitance that varies with a permittivity of a liquid flow line within a dialysis system; wherein the liquid flow line is positioned within the dialysis system;
    a capacitance sensor measuring a capacitance between the first conductive plate and the second conductive plate; and
    the control system programmed to determine a presence of one or more gas bubbles within the liquid flow line based on the capacitance between the first conductive plate and the second conductive plate; the control system operating to divert liquid flow away from the liquid flow line in the dialysis system in response to the capacitance sensor detecting a capacitance which drops below a predetermined value.

2. The dialysis system of claim 1, wherein the dialysis system is a peritoneal dialysis system.

3. The dialysis system of claim 2, wherein the gas bubble detector is positioned in a peritoneal dialysis cycler, and wherein the gas bubble is detected based on the permittivity of a peritoneal dialysis fluid transported by the flow line and by a permittivity of air.

4. The dialysis system of claim 1, wherein the first conductive plate and the second conductive plate are made of a conductive metal alloy.

5. A dialysis system, comprising:
a first liquid flow line; and
a gas bubble detector comprising:
   first and second conductive plates forming a capacitor with a capacitance that varies with a permittivity of the liquid flow line, and
   a capacitance sensor measuring the capacitance between the first conductive plate and the second conductive plate;
wherein the dialysis system further comprises a housing with a receiving slot; and
wherein either:
   a) the housing comprises a hinged door over the receiving slot; the first conductive plate positioned in the housing adjacent the receiving slot and the second conductive plate positioned in the hinged door; or
   b) wherein the receiving slot comprises a slidable tray for a first or a second dialysis cassette; with either the first conductive plate and second conductive plate positioned inside the receiving slot and the other of the first conductive plate and second conductive plate positioned on the slideable tray.

6. The dialysis system of claim 5, further comprising a control system programmed to determine a presence of one or more gas bubbles within the liquid flow line based on the capacitance between the first conductive plate and the second conductive plate.

7. The dialysis system of claim 6, wherein the control system is programmed to provide an alert when a volume of the one or more gas bubbles determined to be present exceeds a predetermined volume.

8. The dialysis system of claim 7, wherein the control system is programmed to automatically modify operation of the dialysis system when the volume of the one or more gas bubbles detected by the gas bubble detector exceeds a predetermined volume.

9. The dialysis system of claim 5, wherein the dialysis system is a peritoneal dialysis system.

10. The dialysis system of claim 9, wherein the gas bubble detector is positioned in a cycler of the peritoneal dialysis system.

11. The dialysis system of claim 5, further comprising a first dialysis cassette, wherein the first liquid flow line is within the first dialysis cassette.

12. The dialysis system of claim 11, the dialysis system further comprises a second dialysis cassette having a second liquid flow line; the first and second conductive plates positioned on components of the system outside the first and second dialysis cassettes.

13. The dialysis system of claim 11, wherein the dialysis system comprises the hinged door over the receiving slot; the first conductive plate positioned in the housing adjacent the receiving slot and the second conductive plate positioned in the hinged door.

14. The dialysis system of claim 11, wherein the dialysis system comprises the slidable tray for the first or second dialysis cassette; wherein either of the first conductive plate and second conductive plate is positioned inside the receiving slot and the other of the first conductive plate and second conductive plate positioned on the slideable tray.

15. A method of using the dialysis system of claim 5, the method comprising the steps of:
   detecting a capacitance between the first conductive plate and the second conductive plate during a dialysis treatment; and
   determining the presence of one or more gas bubbles in the first liquid flow line based on the detected capacitance.

16. The method of claim 15, wherein the step of determining the presence of one or more gas bubbles in the first liquid flow line is performed by a control system of the dialysis system.

17. The method of claim 15, further comprising the step of providing an alert if the detected capacitance drops below a predetermined value.

18. The method of claim 15, further comprising the step of stopping the dialysis treatment if the detected capacitance drops below a predetermined value.

19. The method of claim 15, further comprising the step of modifying operation of the dialysis system to divert liquid flow away from the first liquid flow line if the detected capacitance drops below a predetermined value.

* * * * *